(12) United States Patent
Kader et al.

(10) Patent No.: US 9,272,160 B2
(45) Date of Patent: Mar. 1, 2016

(54) TETHERED AND/OR VISUALLY CODED BRACHYTHERAPY DEVICES AND RELATED METHODS

(75) Inventors: Andrew Karim Kader, San Diego, CA (US); Daniel B. Fried, Spartanburg, SC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 182 days.

(21) Appl. No.: 13/197,345

(22) Filed: Aug. 3, 2011

(65) Prior Publication Data

US 2012/0065454 A1   Mar. 15, 2012

Related U.S. Application Data

(60) Provisional application No. 61/375,289, filed on Aug. 20, 2010.

(51) Int. Cl.
*A61N 5/10* (2006.01)
*A61B 17/34* (2006.01)
*A61B 17/00* (2006.01)
*A61B 19/00* (2006.01)

(52) U.S. Cl.
CPC .......... *A61N 5/1001* (2013.01); *A61B 17/3468* (2013.01); *A61B 2017/00274* (2013.01); *A61B 2017/3411* (2013.01); *A61B 2019/444* (2013.01); *A61B 2019/5487* (2013.01); *A61N 2005/1009* (2013.01); *A61N 2005/1012* (2013.01); *Y10T 29/49826* (2015.01)

(58) Field of Classification Search
CPC . A61N 5/1001; A61N 5/1007; A61N 5/1027; A61N 2005/1008; A61N 2005/1009; A61N 2005/101; A61N 2005/1011; A61N 2005/1012; A61N 2005/1018; A61N 2005/1019; A61N 2005/1024; A61N 2005/1025; A61N 2005/1027; A61M 37/0069; G21G 4/06; G21G 4/08
USPC .................................................. 600/3, 7–8
See application file for complete search history.

(56) References Cited

U.S. PATENT DOCUMENTS

| | | | |
|---|---|---|---|
| 4,642,096 A | 2/1987 | Katz | |
| 5,012,357 A * | 4/1991 | Schoeppel et al. | 378/65 |
| 6,036,632 A | 3/2000 | Whitmore, III et al. | |
| 6,554,760 B2 * | 4/2003 | Lamoureux et al. | 600/7 |
| 6,572,525 B1 * | 6/2003 | Yoshizumi | 600/7 |
| 6,579,262 B1 | 6/2003 | Mick et al. | |
| 6,652,442 B2 * | 11/2003 | Gatto | 600/3 |

(Continued)

FOREIGN PATENT DOCUMENTS

WO   WO 2009/151876   12/2009

OTHER PUBLICATIONS

International Search Report and Written Opinion for corresponding PCT application No. PCT/US2011/046413, date of mailing Mar. 19, 2012.

(Continued)

*Primary Examiner* — Charles A Marmor, II
*Assistant Examiner* — Thaddeus Cox
(74) *Attorney, Agent, or Firm* — Myers Bigel & Sibley, P.A.

(57) ABSTRACT

Bracytherapy devices include a respective tether attached to a proximal end portion of the strands. The tether can be color-coded to match a color associated with the corresponding strand.

14 Claims, 8 Drawing Sheets

(56) References Cited

U.S. PATENT DOCUMENTS

| | | | |
|---|---|---|---|
| 6,761,680 B2 | 7/2004 | Terwilliger et al. | |
| 6,997,862 B2 | 2/2006 | Terwilliger et al. | |
| 7,211,039 B2 | 5/2007 | Lamoureux | |
| 7,601,113 B2 | 10/2009 | Lebovic et al. | |
| 7,736,292 B2 | 6/2010 | Hermann et al. | |
| 2003/0109769 A1* | 6/2003 | Lowery et al. | 600/7 |
| 2004/0116767 A1* | 6/2004 | Lebovic et al. | 600/7 |
| 2004/0242953 A1* | 12/2004 | Good | 600/7 |
| 2007/0167664 A1* | 7/2007 | Hermann et al. | 600/3 |
| 2007/0270627 A1* | 11/2007 | Cutrer et al. | 600/7 |
| 2008/0166681 A1* | 7/2008 | Weinstein et al. | 433/76 |
| 2008/0288068 A1* | 11/2008 | Kronowitz | 623/8 |
| 2009/0209804 A1* | 8/2009 | Seiler et al. | 600/7 |
| 2010/0016710 A1* | 1/2010 | Kumar et al. | 600/425 |
| 2010/0041938 A1* | 2/2010 | Stoianovici et al. | 600/7 |
| 2011/0105823 A1* | 5/2011 | Single et al. | 600/3 |

OTHER PUBLICATIONS

RAPID Strand™, Oncura Inc. Product description, http://www.oncura.net/brachytherapy-rapid-strand.php, Copyright 2008, printed from the internet Mar. 16, 2010, date unknown but believed to be prior to the priority date of the above referenced application, 3 pages.

* cited by examiner

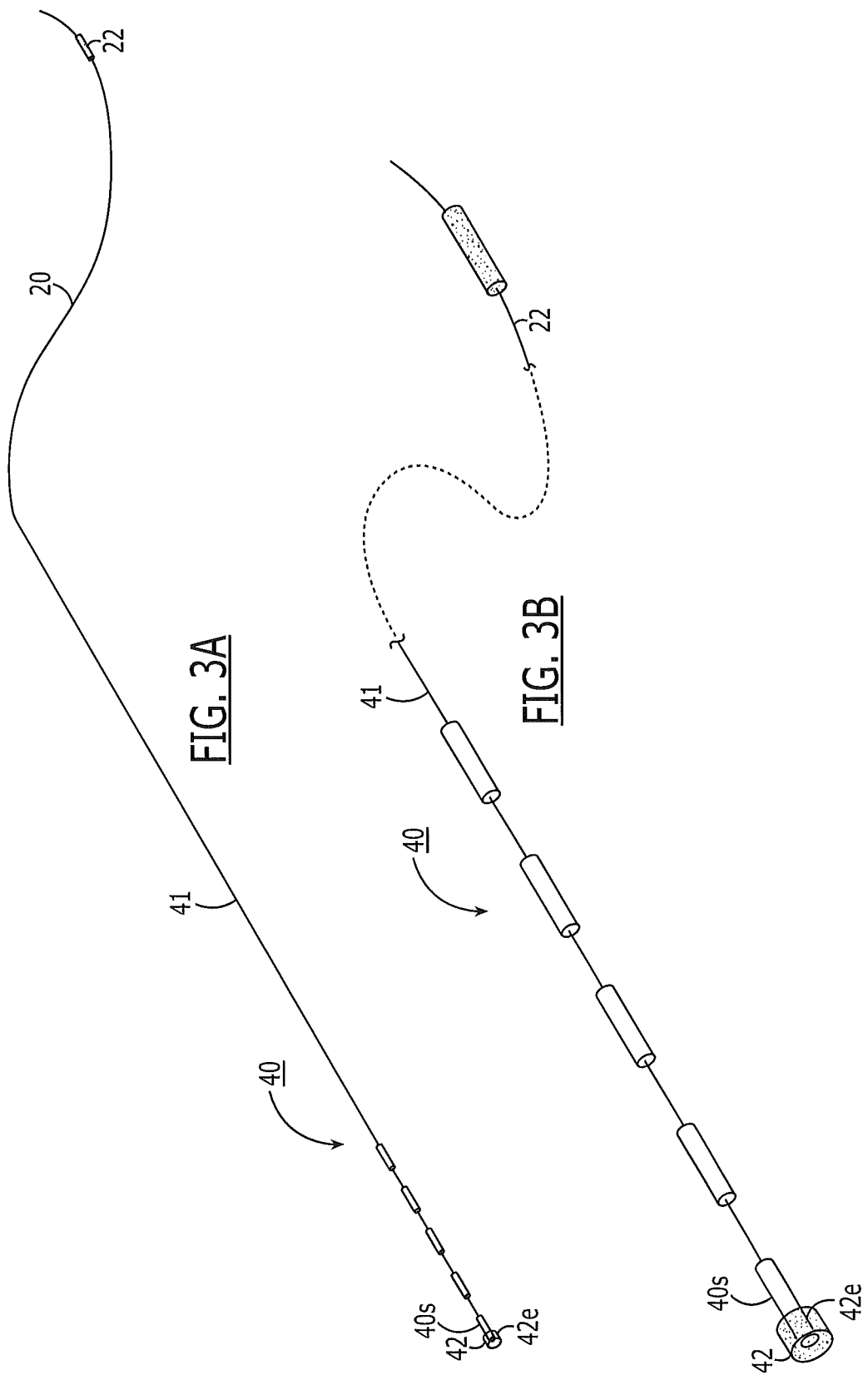

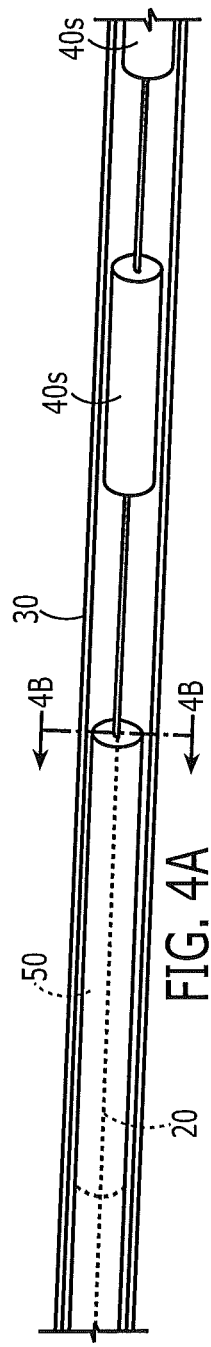
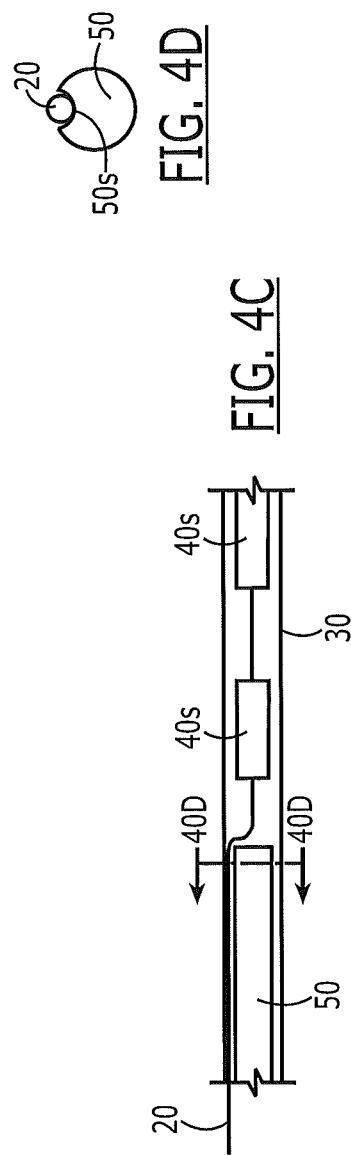
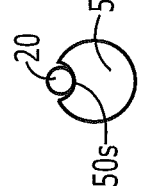
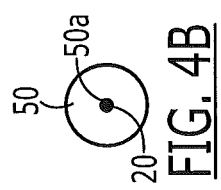
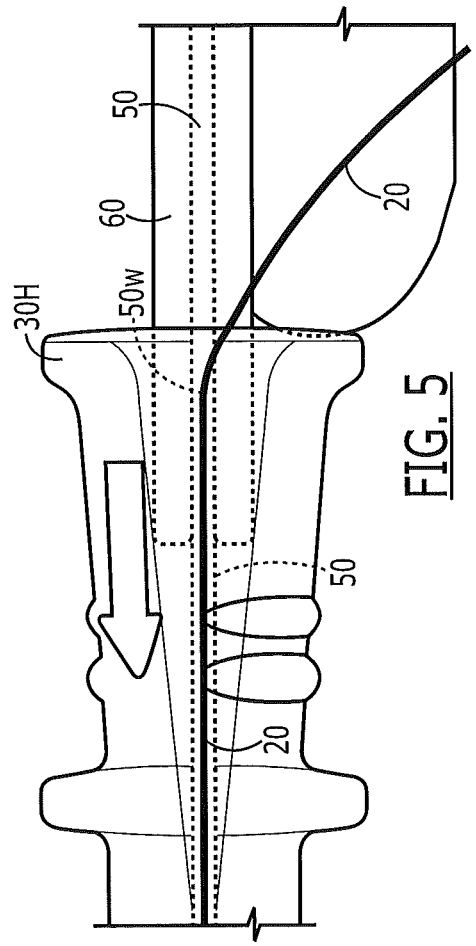
FIG. 4A
FIG. 4B
FIG. 4C
FIG. 4D
FIG. 5

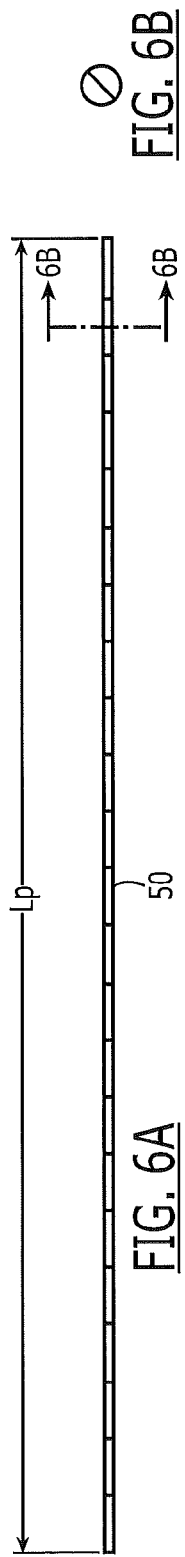
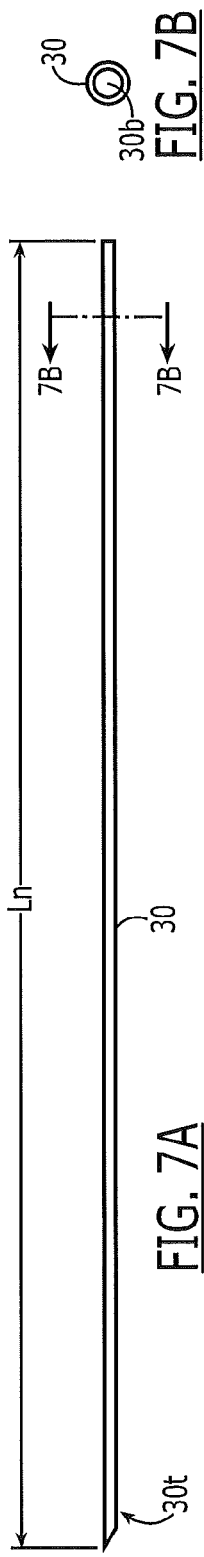
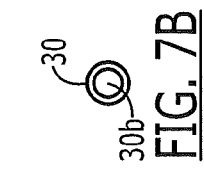
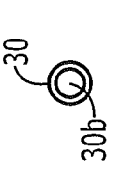
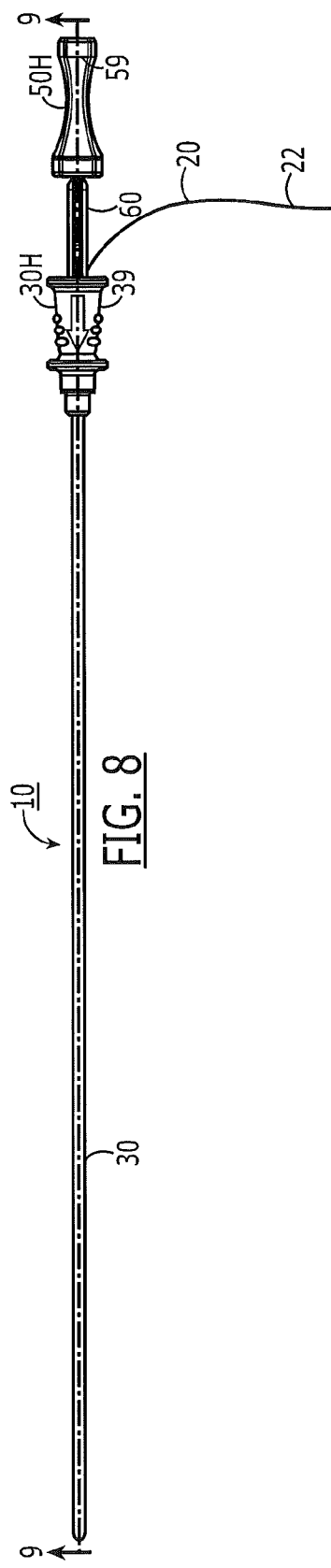

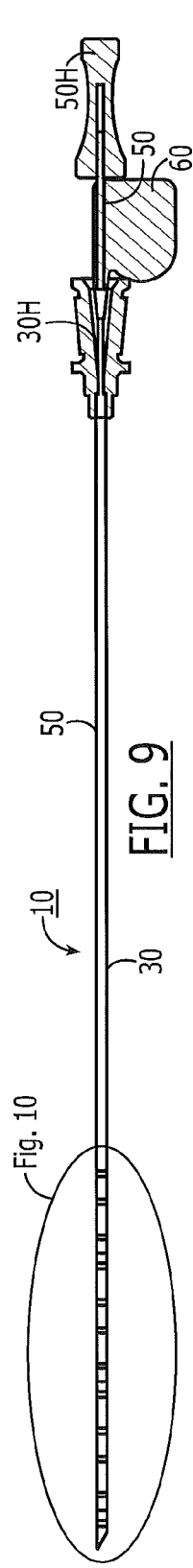
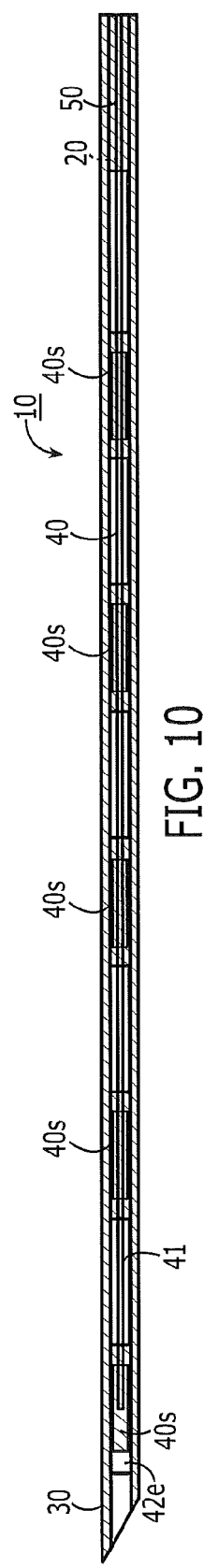
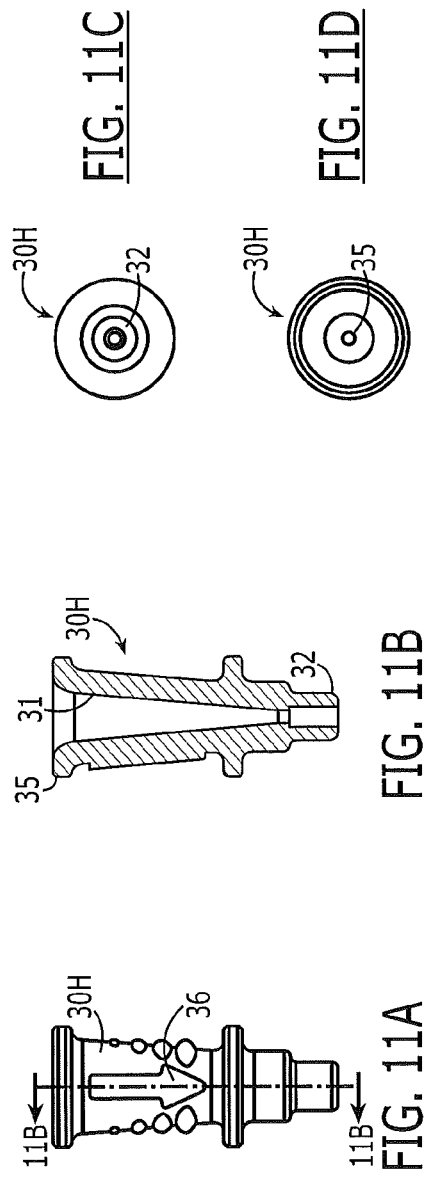
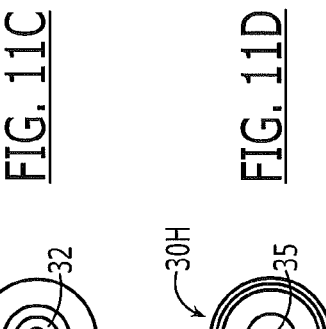

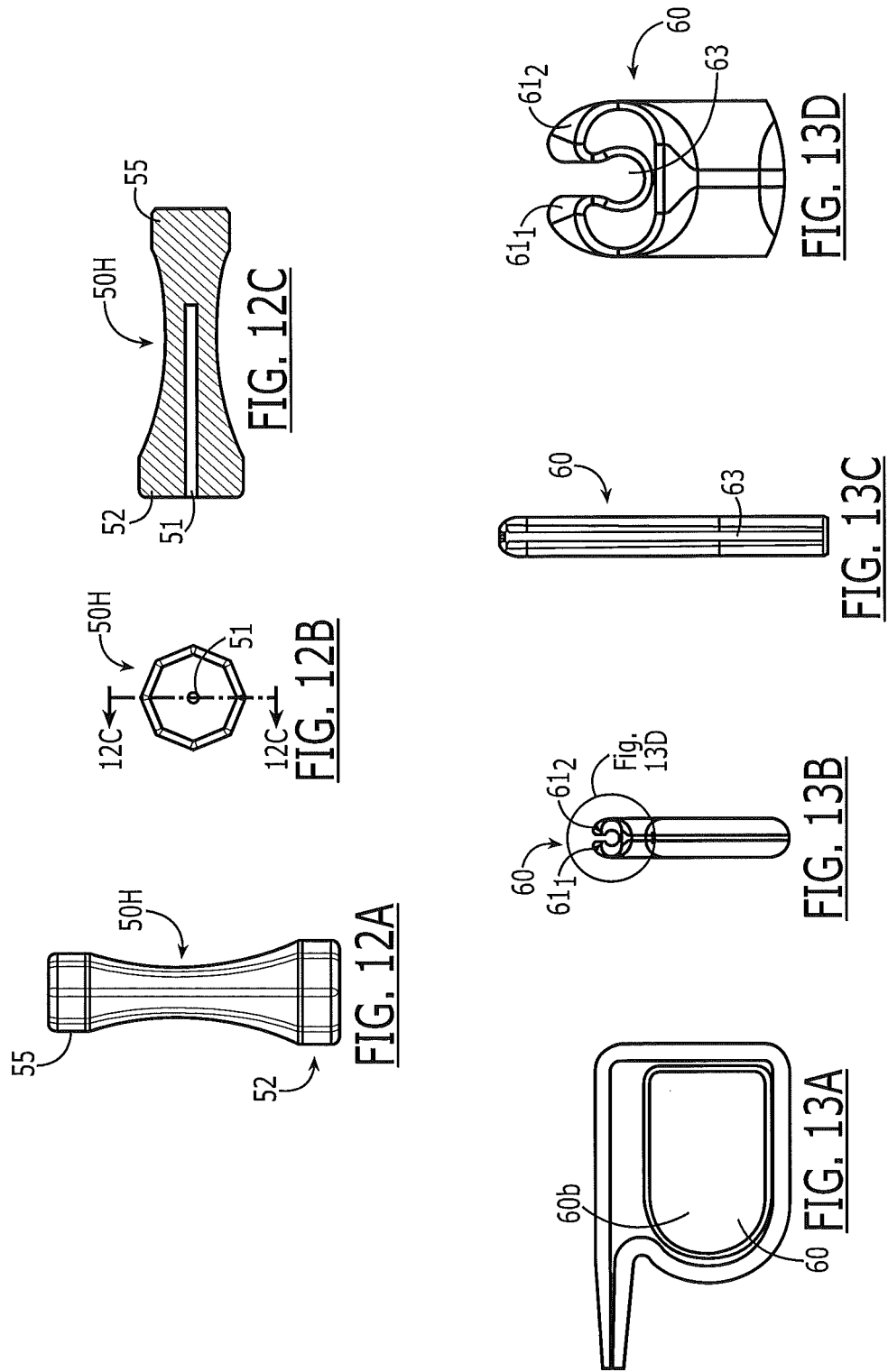

TETHERED AND/OR VISUALLY CODED BRACHYTHERAPY DEVICES AND RELATED METHODS

RELATED APPLICATIONS

This application claims the benefit of and priority to U.S. Provisional Application Ser. No. 61/375,289 filed Aug. 20, 2010, the contents of which are hereby incorporated by reference as if recited in full herein.

FIELD OF THE INVENTION

This invention relates to surgical devices.

BACKGROUND OF THE INVENTION

Currently, small brachytherapy seeds are placed at defined intervals along a suture strand and placed into the prostate to treat a patient with prostate cancer. Several rows of seeds are typically implanted and several strands of seeds are used per row. An example of such a device is the RAPID Strand™ suture available from Oncura Inc., Arlington Heights, Ill., which is described as an absorbable braided suture containing 10 evenly spaced oncology radioactive seeds (Iodine-125). See also, U.S. Pat. Nos. 6,761,680, 6,997,862 and 7,211,039, the contents of which are hereby incorporated by reference as if recited in full herein. The brachytherapy strands of seeds are typically used for treating prostate cancer but can be used to treat other cancers as well.

Despite the foregoing, there remains a need for improved brachytherapy strands and/or delivery systems that can allow for one or more of: identification, removal, and/or redeployment of improperly positioned brachytherapy seeds.

SUMMARY OF EMBODIMENTS OF THE INVENTION

Embodiments of the invention are directed to brachytherapy strands with radioactive seeds and an attached tether extending from a proximal end portion thereof. The tether can be used for at least one of the identification, removal and/or redeployment of (improperly positioned) brachytherapy seeds.

Embodiments of the invention provide strands with visual indicia that corresponds to visual indicia on the tether, e.g., color-coded ends and/or portions of strands, for ease of visual recognition during and/or after placement in a target intra-body location.

Embodiments of the invention provide an injector/plunger that resides in a delivery needle and accommodates passage of the tether at the time of deployment (either with an axially extending through-aperture or bore, outer slot or size clearance).

Embodiments of the invention provide visual indicia for each strand of seeds or for a particular row or column of seeds that can be visually and/or electronically identified. Where used, the electronic identification can comprise image recognition to provide the location of the corresponding strand in the target tissue, correlated to the visual (color-coded) indicia of the strand.

Embodiments of the invention are particularly useful for prostate brachytherapy treatments.

Some embodiments are directed to brachytherapy devices. The devices can include an implantable strand with radioactive material and a tether attached to a proximal end portion of the strand.

The tether can optionally include visual indicia. The readioactive material can include seeds, and at least a distal seed of the strand can have a color that corresponds to a color associated with the tether. The tether may be color-coded to match a color associated with the strand.

The brachytherapy device can be used in combination with a second brachytherapy device (and typically many more than two, such as between about 10-60). The second brachytherapy device also includes an implantable strand with radioactive material and a tether extending from and/or attached to a proximal end portion of the strand. The first device strand and the second device strand can have different color tethers.

Yet other embodiments are directed to brachytherapy assemblies. The assemblies include: (a) a needle; (b) a strand with radioactive material residing in a distal end portion of the needle, the strand further comprising a tether that extends upstream of the radioactive material; and (c) a plunger residing in the needle configured to slidably hold the tether.

The tether and the strand can optionally include corresponding visual indicia.

The strand radioactive material may include a plurality of spaced apart radioactive seeds, and the tether and at least a distal seed can be color-coded.

The plunger can include a longitudinally extending bore and/or slot that receives the tether therein.

The tether can have a length sufficient to extend inside the needle to exit at a proximal portion of the needle and extend a distance beyond the needle.

The tether may reside in a center bore of the plunger inside the needle and exit the plunger and needle at a location that is proximate a handle associated with the needle.

The needle can include a needle handle at a proximal portion thereof and the plunger can include a plunger handle at a proximal portion thereof. In operation the plunger handle can slide the plunger a distance into the needle to force the strand with the radioactive material to exit the needle into target tissue.

The assembly may include a deployment guard that releasably resides between the needle handle and the plunger handle prior to active deployment.

The deployment guard can include a pair of arms that define a longitudinally extending channel that releasably holds a stem of the plunger.

At least one of the plunger handle, needle handle and tether can be color-coded to the strand and/or at least one radioactive material associated therewith.

Yet other embodiments are directed to a set of brachytherapy strands. The set includes a plurality of implantable strands of radioactive material, each strand comprising a respective tether. At least one of the tethers has different visible indicia than the others.

The strands can be color-coded to the corresponding tether.

The radioactive material may include a plurality of spaced apart seeds. Each strand comprises a color on a distal radioactive seed that is color-coded to the respective tether.

Still other embodiments are directed to brachytherapy template grids. The grids include a grid body with a set of channels arranged in defined columns and rows. At least one of the rows is configured to have different color indicia than other rows.

Yet other embodiments are directed to methods of carrying out a brachytherapy procedure. The methods include: (a) providing a needle with a strand of radioactive material having a tether and a plunger; (b) pushing the plunger; (c) slidably extending the plunger in the needle in response to the pushing step; and (d) forcing the radioactive material out of the needle based on the extending step while retaining the tether remains attached to the strand with a portion in the needle and a proximal portion extending outwardly therefrom.

The method can include pulling the tether toward the needle handle to retract the strand of radioactive material back into the needle.

The method can include slidably extending the tether through a slot or bore in the plunger a distance substantially equal to a distance the radioactive strand travels during the forcing step.

The method can include visually comparing visual indicia on the strand of radioactive material to corresponding visual indicia on the tether to identify a strand associated with a radioactive seed that is in an undesired location in the body.

Still other embodiments are directed to methods of fabricating a brachytherapy strand. The methods include (a) providing a strand of radioactive material; and (b) attaching a tether to a proximal end portion of the strand or forming the strand to define a longitudinally extending tether with a length that extends outside the body when the radioactive material is in the implanted position.

The method can include placing color indicia on the strand of radioactive material and placing corresponding color indicia on the tether.

The foregoing and other objects and aspects of the present invention are explained in detail in the specification set forth below.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 3A is a side perspective view of a strand of radioactive seeds with a tether according to embodiments of the present invention.

FIG. 3B is an enlarged view of the opposing end portions of the strand and tether shown in FIG. 3A according to embodiments of the present invention.

FIG. 4A is an enlarged side view of a needle (shown transparent) encasing an injector/plunger and tether.

FIG. 4B is a section view taken along line 4B-4B in FIG. 4A.

FIG. 4C is a side section view of a portion of a needle encasing an injector/plunger and tether according to other embodiments of the present invention.

FIG. 4D is a section view taken along line 4D-4D in FIG. 4C.

FIG. 5 is a greatly enlarged side view of the device shown in FIG. 1 with certain components shown substantially transparent and illustrating a proximal exit path for a tether according to embodiments of the present invention, FIG. 6A is a side view of an exemplary plunger/injector (without the handle) according to embodiments of the present invention.

FIG. 6B is a section view taken along line 6B-6B in FIG. 6A.

FIG. 7A is a side view of an exemplary delivery needle according to embodiments of the present invention.

FIG. 7B is a section view taken along line 7B-7B in FIG. 7A.

FIG. 8 is a side view of a delivery assembly according to embodiments of the present invention.

FIG. 9 is a section view taken along lines 9-9 in FIG. 8.

FIG. 10 is an enlarged detail section view of the portion of the device shown in FIG. 8.

FIG. 11A is a top view of an exemplary handle for the needle according to embodiments of the present invention.

FIG. 11B is a section view taken along line 11B-11B in FIG. 11A,

FIG. 11C is a distal end view of the device shown in FIG. 11A.

FIG. 11D is a proximal end view of the device shown in FIG. 11A.

FIG. 12A is a top view of an exemplary plunger/injector handle according to embodiments of the present invention.

FIG. 12B is a distal end view of the device shown in FIG. 12A.

FIG. 12C is a section view taken along line 12C-12C in FIG. 12B.

FIG. 13A is a side view of a deployment guard according to embodiments of the present invention.

FIG. 13B is an end view of the device shown in FIG. 13A.

FIG. 13C is a top view of the device shown in FIG. 13A.

FIG. 13D is an enlarged view of a portion of the device shown in FIG. 13B.

DESCRIPTION OF EMBODIMENTS OF THE INVENTION

Figure 1:
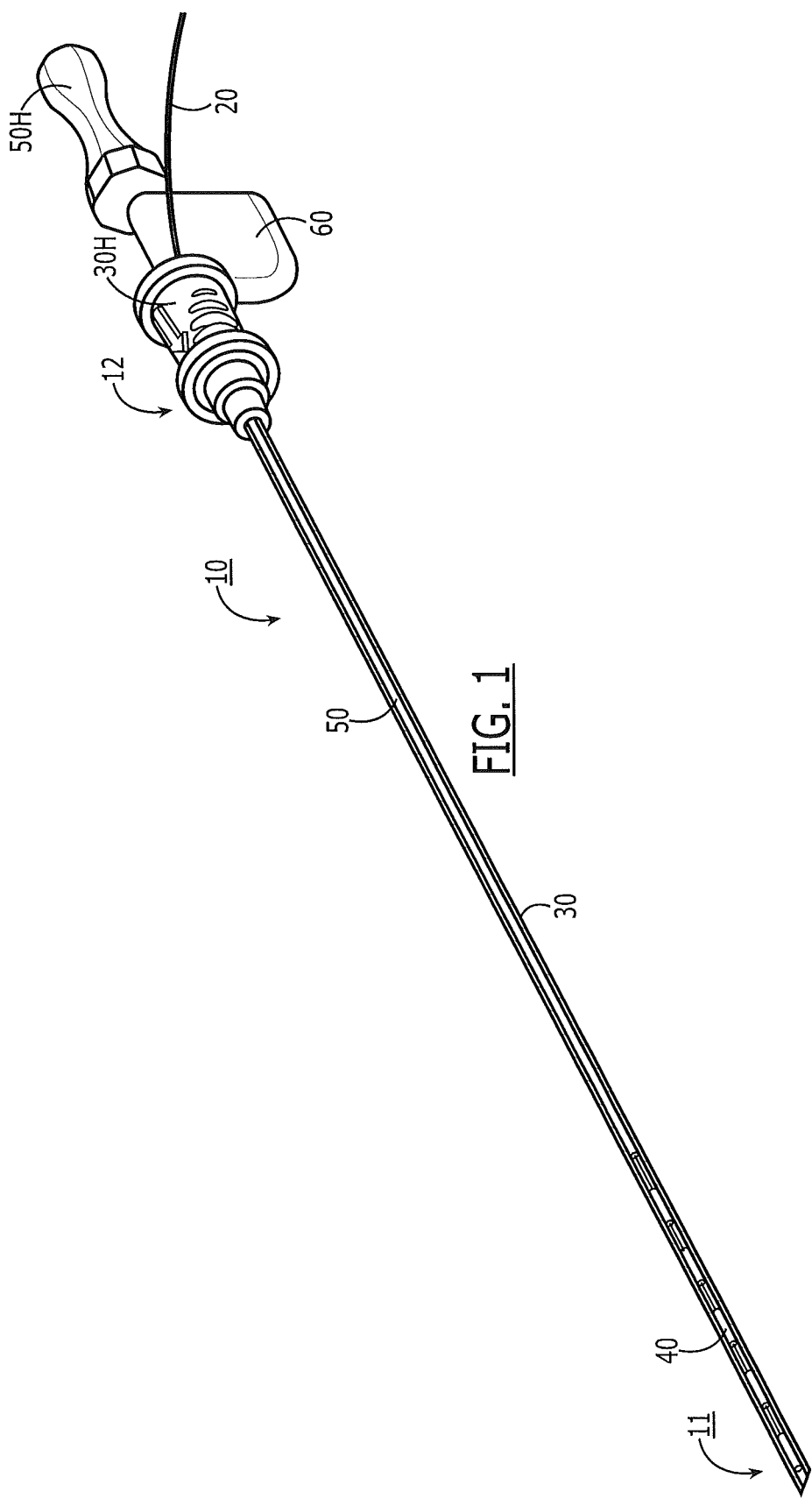
FIG. 1 is a side perspective view of an exemplary surgical delivery device according to embodiments of the invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments. The term "distal" refers to a direction or location that is closer to or toward a patient while the term "proximal" refers to the opposing direction or a location that is further away from the patient.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein.

The term "color-coded" means that the so-called components have a color that is the same or sufficiently similar so that the two components are readily visually identifiable as related.

The term "tether" refers to a flexible thread, suture, wire or other material that extends a length off a proximal end portion of an implantable brachytherapy strand that holds radioactive material (typically at least one radioactive seed, and more typically a plurality of spaced apart radioactive seeds) thereon. However, the radioactive material may be provided in other ways. The word "strand" refers to a flexible (typically implantable) biocompatible suture or other material (thread, filament and/or wire), typically a multi-suture (e.g., braided suture) configuration that holds radioactive material, e.g., seeds, in longitudinally spaced apart positions (in contrast to "loose seeds"). The strand can be axially stiff, while being radially flexible or may have other characteristics. See, e.g., U.S. Pat. Nos. 6,761,680 and 6,997,862 to Terwilliger et al., the contents of which are hereby incorporated by reference as if recited in full herein. The tether can be an extension of the strand or may be a separate material, such as a different suture material that extends a length beyond that of the strand, typically a length sufficient to extend upstream of the strand to the proximal end of the needle and more typically a length sufficient to extend 1-12 inches beyond of the delivery needle. If the latter, the tether can be attached to the strand in any desired manner, e.g., fused, tied, molded, or adhesively attached or attached using a clip, staple, friction, molded or via a mechanical clamp or other component. The tether may be a single monofilament suture or may be a multi-filament suture, including a braided suture.

The phrases "visual indicia" or "visible indicia" are used interchangeably and refer to an optically (typically visually) recognizable color, pattern and/or alphanumeric marking. The visual indicia can be color alone, color and pattern, pattern with the same color, or alpha numeric indicia alone or with color, or any combination of the above or other visually detectable features (typically visually detectable without magnification with normal eyesight). The visual indicia may comprise (gold) markers that are identifiable via X-ray or ultrasound. For example, for a particular procedure between about 10-60 strands may be deployed (typically using a template with columns and rows for placement) for the dosing plan in the prostate. Each tether or sets of tethers for a particular use can comprise a different color (or different hues or intensity of color). Alternatively, some or even all of the tethers for a particular use may have the same color but may include a different pattern such as a different number and/or alpha indicator, dots, stripes, lines, geometric shapes or non-geometric shapes, combinations thereof or other visually distinguishable features. Preferably, each tether, each row or column of tethers, or spatially related tethers can have a visually different color for faster visual recognition as to which associated strand/seed is in a particular (e.g., improper) location. Each tether 20 (FIGS. 1-2) can be attached to a respective strand that can also include corresponding visual indicia (e.g., color) that corresponds to the associated tether.

Figure 2:
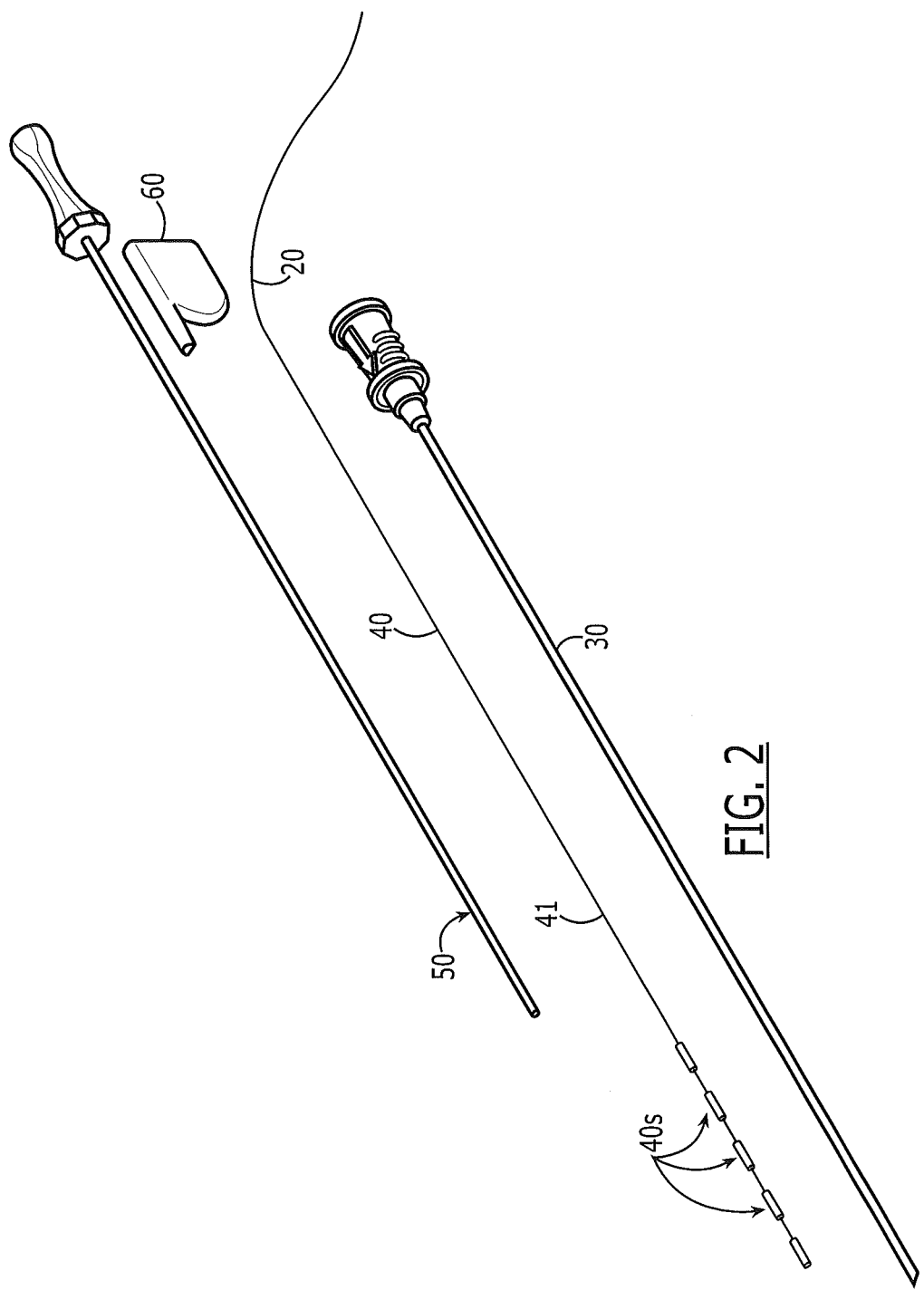
FIG. 2 is an exploded view of the device shown in FIG. 1.

FIGS. 1 and 2 illustrate a surgical delivery assembly 10 having distal and proximal end portions 11, 12, respectively, with a tether 20 extending from the proximal end portion 12. The assembly 10 includes a needle 30 that holds the strand of radioactive material 40 (e.g., a suture 41 with spaced apart radioactive seeds 40s). The assembly 10 also includes a plunger 50 (also known as an injector or ejector) that extends through the needle 30 to expel or push the radioactive material 40 (e.g., radioactive seeds) into position in target tissue (e.g., the prostate). The assembly 10 can also optionally include a releasable deployment guard 60 to inhibit undesired ejection of the radioactive material prior to insertion.

In particular embodiments, the tether 20 is biodegradable (as can be the strands 41). In conventional designs, once the strands 40 are implanted, there are limited viable options to remove them except in a relatively invasive manner. In contrast, the tether 20 allows the strand 41 to be pulled out and re-positioned. The delivery assembly 10 can be configured to accommodate the tether 20.

In particular embodiments, the strands 41 and tethers 20 can be color-coded or otherwise configured with corresponding visible indicia 42, 22, respectively, that identifies that a respective pair is related. Unfortunately, a relatively common mistake in conventional brachytherapy procedures occurs when a strand gets undesirably close to the urethra, urethral sphincter, bladder, rectum, neurovascular bundle or placed in an area that does not allow for desirable (e.g., increased or maximum) cancer control. For example, one or more strands or seeds may be pushed through the prostate and into the bladder or rectum. While one can go into the bladder with an endoscope and see that there is a strand extending into the bladder, it is difficult to tell which of the plurality (typically between 10-20 or more) strands 41 is causing the problem. In addition, there is no easy way to get it out without the tether 20.

FIG. 3A illustrates that the tether 20 can optionally include visual indicia 22. In some embodiments, the handle 30H and/or 50H may alternatively or additionally include corresponding visual indicia 39, 59, respectively (FIG. 8). The visual indicia 22 (and/or 39, 59) can be provided by a color, pattern or other marking of the tether 20 itself (all or a portion of the entire length of the tether) such as by a filament, strand or body of the tether or by a component integrally or releasably attached to the tether 20, such as a clip, paper, elastomeric tag, end cap, sleeve, block body or other device (that can reside a distance away from the proximal end of the tether). The tether 20 can have a smaller diameter or size than that of the strand 41 of the radioactive implant 40. In other embodiments, the tether 20 can have substantially the same cross-sectional size (and can be round or have another shape). The tether 20 can also optionally have different shapes or sizes over different segments (not shown). The tether 20 can have a length that is at least a major portion of the length of the needle 30, e.g., with a length sufficient to extend out a distance beyond the handle 30H while being attached to the proximal end of the strand 41. In particular embodiments, the tether 20 has a length that is between about 100 mm to about 500 mm, more typically between about 100-300 mm.

FIG. 3A illustrates that a distal end portion of the strand 40 can include visible indicia 42 such as an end cap 42e that has a color that corresponds to a color and/or other visible indicia 22 on the tether 20. The visible indicia 42 may alternatively be placed on the strand/suture 41 upstream of the end seed 40s or at both and/or other locations or extend the entire length of the suture 41 and/or on one or more seeds 40s and the like. The visible indicia 42 can be provided by using a biocompatible color coating, seed material or encasement material for the seed (e.g., colored titanium), and/or by painting, dyeing or otherwise providing the seed and/or strand thereat with an externally visible color that can be distinguished from at least one other strand of radioactive material (e.g., seeds 40s). For example, a small (e.g., about 1-5 mm, typically about 2.5 mm) distal color-coded end cap be placed on the most distal seed. The color can correspond to a particular row in a grid (see, e.g., FIG. 14) such as "red" for the most anterior row. The visual indicia 42 can be used so that at the time of cytoscopy, those strands 40 extending into the bladder or at other undesired locations can be more easily distinguished from one another. FIG. 3B illustrates that the tether visual indicia 22 can include a color-coded "rope" or "string" and/or a proximal sleeve that can be color-coded to a corresponding distal seed and/or strand visual indicia 42 such as by color coding an end cap, end seed and/or strand thereof 42e (shown by the shading).

FIGS. 4A and 4B illustrate that the plunger/injector 50 can include an axially extending bore 50a (typically a center bore) that defines a channel for the tether 20. FIGS. 4C and 4D illustrate that the tether 20 can be held against an outer surface of the plunger 50. As shown in FIG. 4D, the tether 20 can optionally be held in a slot 50s formed in an outer wall of the plunger 50 for allowing the tether 20 and seeds 40s to be slidably deployed from the needle 30. In other embodiments, the tether 20 can be held between the plunger outer wall and the needle inner wall based on a snug clearance fit sized to allow the tether to slidably extend. The needle bore may optionally be stepped to have a smaller size downstream of the tether (proximate the seeds 40s) to provide a desired snug fit for proper alignment at discharge while accommodating the tether 20 upstream of the seeds 40s.

FIG. 5 illustrates that the tether 20 can be configured to extend through the needle handle 30H a distance, then extend outside of the plunger 50 and needle handle 30H at a proximal portion thereof. Thus, the plunger 50 can include an exit window 50w downstream of the plunger handle proximate the needle handle (in the non-deployed position). However, other the assembly 10 can provide for other tether 20 exit locations.

FIGS. 6A and 6B illustrate an exemplary plunger 50 (without the handle 50H). The plunger 50 may have a length "Lp" that is less than a length "Ln" of the needle 30, such as between about 5-15 mm less and more typically about 12 mm less for a plunger having a length of about 146 mm. The diameter of the plunger 50 is typically small (e.g., about 0.66 mm or less) and is sized to slidably snugly reside in the bore of the needle 30.

FIGS. 7A and 7B illustrate an example of a needle 30 (without the handle). The needle can have an angled tip 30t and a bore 30b. The needle 30 can be any suitable size and typically has an OD (outer diameter) that is less than about 1.3 mm and an ID (inner diameter) that is about 0.84 mm. The needle 30 can be any suitable length, but is typically between about 158 mm to about 159 mm.

FIGS. 8-10 illustrate the device 10 with the needle 30, the plunger 50, the tether 20 and the seeds 40s assembled. FIG. 8 also illustrates that the handle 30H and/or 50H may include corresponding visual indicia 39, 59 that corresponds to the tether indicia 22 and seed indicia 42.

FIGS. 11A-11D illustrate an exemplary needle handle 30H with a tapered bore 31 for slidably receiving the plunger 50. The handle 30H has a proximal end 35 and a distal end portion 32. The handle 30H may also include an arrow 36 to indicate that a clinician should slide the plunger 50 in that direction to eject the radioactive seeds 40s (after removing the guard 60).

FIGS. 12A-12C illustrate an exemplary plunger handle 50H. The handle includes a receiving bore 51 for holding an end portion of the plunger body 50. The handle 50H includes opposing proximal and distal end portions, 52, 55, respectively.

FIGS. 13A-13D illustrate an exemplary deployment guard 60. As shown, the guard 60 can include a pair of arms $61_1$, $61_2$ that define an axially or longitudinally extending channel 63 therebetween that releasably engage the plunger 50. The guard 60 resides between the needle handle 30H and the plunger handle 50H and holds a length of the plunger 50 in the channel 63 to block any longitudinally sliding movement of the plunger 50 prior to use. The arms $61_1$, $61_2$ and channel 63 can extend in the longitudinal direction a distance of between about 15-25 mm, typically about 19 mm (such as about 19.05 mm) which can substantially correspond with (e.g., be substantially the same as) the stroke distance of the plunger 50 during use. The guard 60 can have a substantially planar primary body 60b that can be easily grasped for removal during use.

Figure 14:
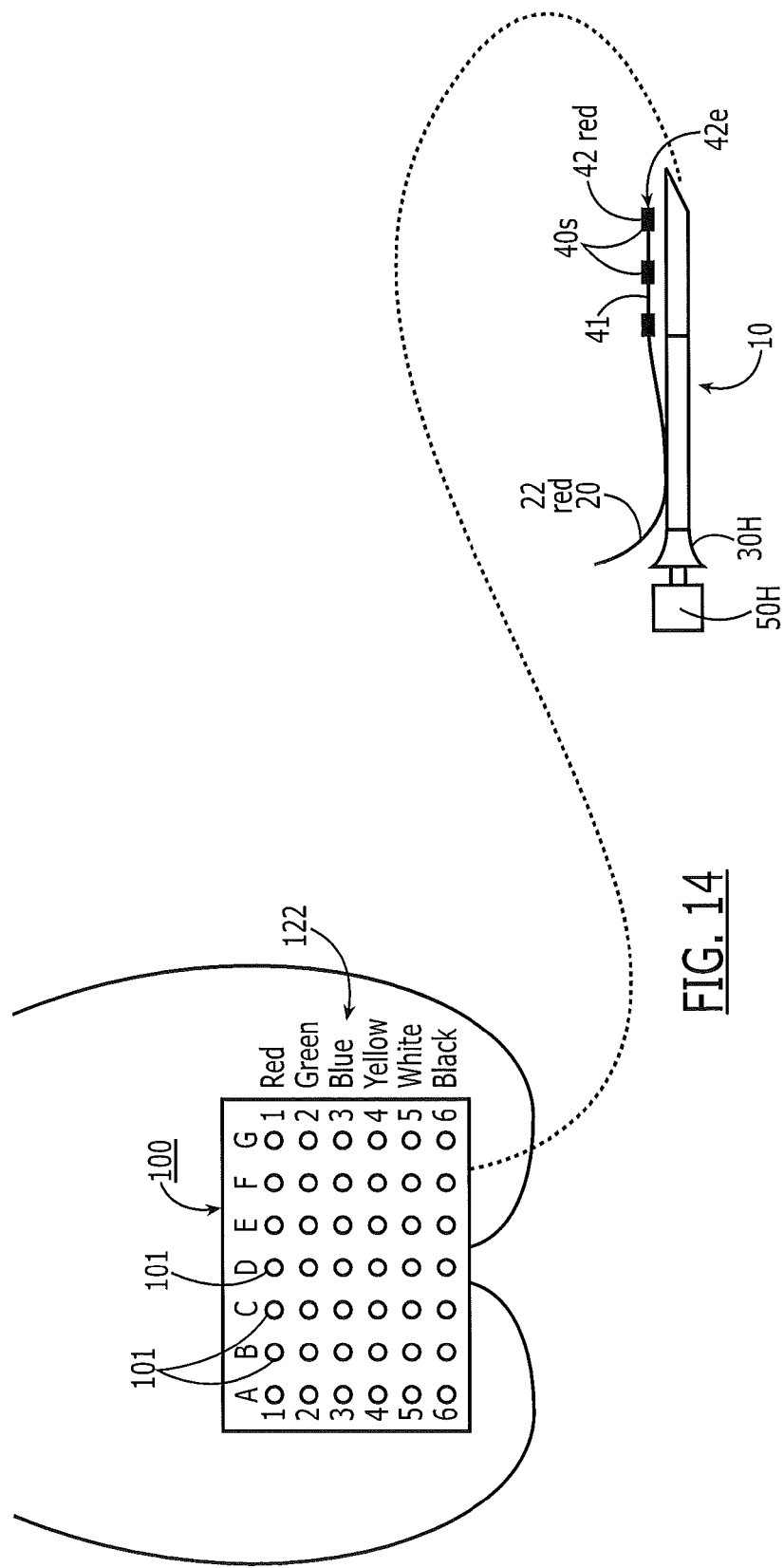
FIG. 14 is an example of a template grid.

FIG. 14 illustrates a template grid 100 which can comprise visual indicia 122 that corresponds to the tether indicia 22 and/or strand 41 and/or seed 40s (e.g., be color-coded). For example, the grid 100 can be configured so that each of the outer wall or each entry channel 101 associated with a particular row/column can include the indicia 122, e.g., each channel or wall adjacent thereto can be color coded to correspond with the desired strand/tether color.

FIG. 14 also illustrates that the delivery device 10 can be pre-loaded with the suture/strand and seeds 40 and tether 20, and the tether 20 and distal end portion of the radioactive material/strand 40 can be color-coded (each can be red). The needle or handles 30H, 50H may also optionally be color-coded to correspond with the tether 20 and/or strand/seed 40s, 41. During use, a clinician can insert the strand/needle assembly 10 into the correct color coded row or column (shown as each row being color coded). As shown by way of example only, a device 10 comprises "red" visible indicia 42 and 22 and is intended to be inserted into the grid at the row with the corresponding visible indicia 122, e.g., the "red" row.

It is contemplated that each row may have the same color but each column in that row may have some visual distinctive/unique identifier. For example, all strands on the most anterior row can have a red end cap, but one end cap may be solid while another may be striped. Different patterns or color demarcation (all being red) may help a user visually and faster identify which strand should be pulled (e.g., solid red strand means it is in the anterior row, while striped red means it is in column B"). Thus, the indicia 22, 42 for each grid row of strands 40 may have a common color and the indicia 22, 42 for each grid column may have a common pattern. The grid 100 can include corresponding indicia 122 unique for each row and column.

It is contemplated that the color-coded tethers 20 and/or strands 40 can be provided as a set of individual colors or in groups of different colors with or separate from the grid 100 as a kit or kits of supplies for a surgical procedure.

In some embodiments, the plunger 50 and/or needle 30 can continue to hold the tether 20 (still connected to the strand 41) after the seeds 40s are deployed. If the location is deemed inappropriate, the user can pull the tether 20 outward (away from the body), thereby removing the seeds 40s. It is also contemplated that the user may then reposition those seeds in a needle 30 for easy redeployment (the needle 30 may be the same needle used to deliver the seeds 40s or may optionally be a new needle that cooperates with the plunger 50 and tether 20). Once in proper position, the tether 20 can be cut (typically at the level of the perineal skin) and left in position. The tether 20 can be absorbed by the body over time.

Embodiments of the invention provide visual indicia for each strand of seeds or for a particular row or column of seeds that can be visually and/or electronically identified. Where used, the electronic identification can comprise image recognition to provide the location of the corresponding strand in the target tissue, correlated to the visual (color-coded) indicia of the strand. The electronic identification can be visually displayed on a display or other image for clinician reference.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, if used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A set of brachytherapy assemblies, comprising:
   between 10-60 brachytherapy assemblies, each assembly comprising:
   a needle, wherein the needle comprises a needle handle at a proximal portion thereof;
   a strand with radioactive material residing in a distal end portion of the needle, the strand further comprising a flexible tether that has a length sufficient to reside external of a patient when the strand is in position;
   a plunger residing in the needle configured to slidably hold the tether, wherein the plunger comprises a plunger handle at a proximal portion thereof, wherein the tether and the strand and/or radioactive material of the strand comprise corresponding visual indicia, and wherein the between 10-60 brachytherapy assemblies each comprise different corresponding visual indicia; and
   a deployment guard that releasably resides between the needle handle and the plunger handle prior to active deployment, wherein a portion of the tether extends externally away from the assembly between the needle handle and the plunger handle when the deployment guard is in position, wherein the deployment guard comprises a substantially planar body that resides between and extends a distance below the needle handle and the plunger handle, the deployment guard having one long side with a pair of longitudinally extending closely spaced apart arms that define a longitudinally extending channel that contacts and releasably holds a stem of the plunger,
   wherein, in operation the plunger handle slides the plunger a distance into the needle to force the strand with the radioactive material to exit the needle into target tissue, and wherein a portion of the tether extends externally away from the assembly between the needle handle and the plunger handle when the deployment guard is in position.

2. The assembly of claim 1, wherein the strand radioactive material comprises a plurality of spaced apart radioactive seeds, and wherein the tether and at least a distal seed are color-coded.

3. The assembly of claim 1, wherein the plunger comprises a longitudinally extending bore and/or slot that receives the tether therein.

4. The assembly of claim 1, wherein the tether has a length sufficient to extend inside the needle to externally exit at a proximal portion of the needle and extend a distance outside of the plunger and needle.

5. The assembly of claim 1, wherein the tether resides in a center bore of the plunger inside the needle and exits the plunger and needle at a location that is proximate a handle associated with the needle to have an externally extending length.

6. The assembly of claim 1, wherein at least one of the plunger handle, or needle handle is also color-coded to the tether and strand and/or at least one radioactive material associated therewith.

7. The assembly of claim 1, wherein the corresponding visual indicia comprises a color that also corresponds to a color associated with a respective location in a grid of entry ports in columns and rows entry channels used to insert a respective strand into a patient.

8. The assembly of claim 1, further comprising a grid body with channels arranged in defined columns and rows, wherein at least one of the rows is configured to have a first color that is different than a color or colors of other rows, and wherein the corresponding visual indicia of the tether and the strand and/or radioactive material have the first color.

9. The assembly of claim 1, wherein the visual indicia includes a color that corresponds to a respective single column or row of a grid with entry ports of channels arranged in columns and rows used to insert the strands into a patient.

10. A method of carrying out a brachytherapy procedure, comprising:
    providing between 10-60 needles, each with a strand of radioactive material having a flexible tether, wherein at least ten of the tethers have different colors from each other, and wherein respective tethers and strands and/or tethers and radioactive material have a corresponding color to identify them as attached;
    slidably extending a plunger in the respective needle; and
    forcing the radioactive material out of the respective needle into a patient based on the extending step while a corresponding tether remains attached to the strand and extends through the needle to exit a proximal portion thereof with a length sufficient to extend outwardly and externally away from the needle to thereby visually correlate an external tether with a corresponding internal strand; and after the forcing step, visually comparing the color on the strand of radioactive material and/or on the radioactive material to the color on the tether to identify a strand associated with a radioactive seed that is in an undesired location in the body.

11. The method of claim 10, further comprising pulling the tether toward a needle handle to retract the strand of radioactive material back into the needle.

12. The method of claim 10, further comprising, before the slidably extending, aligning the needles with a grid having an array of grid channels, with channels and/or rows of channels having a color corresponding to at least one of the tether and the radioactive material or the tether and the strand holding the radioactive material, then slidably extending the tether through a slot or bore in a respective plunger a distance substantially equal to a distance the radioactive strand travels as it exits the needle to a desired intrabody position during the forcing step.

13. The method of claim 10, further comprising aligning a needle holding the strand and tether with a grid having an array of grid channels, with channels and/or rows of channels having a color corresponding to at least one of the tether and the radioactive material or the tether and the strand holding the radioactive material, inserting the needle with the strand and tether into a channel having the corresponding color, and wherein the method is repeated a plurality of times to insert different strands with tethers in different channels, wherein the tether and strand have different colors at corresponding to different colors of different rows of the grid.

14. A method of fabricating a brachytherapy strand, comprising:

providing a strand of radioactive material with color indicia; and attaching a flexible tether to a proximal end portion of the strand or forming the strand to define a longitudinally extending flexible tether, wherein the flexible tether has a length with an external free end that extends outside a body of a patient when the radioactive material is in an implanted position and has externally visual color indicia that corresponds to the color indicia of the strand of the radioactive material; and repeating the providing and attaching steps using different color indicia for different tether and strand pairs, and wherein the different color indicia is used for tether/strand pairs having a common radioactive material.

* * * * *